United States Patent
Hsieh et al.

(10) Patent No.: US 12,409,330 B2
(45) Date of Patent: Sep. 9, 2025

(54) AIRTIGHT DEVICE AND FEEDTHROUGH MODULE

(71) Applicant: Wiwynn Corporation, New Taipei (TW)

(72) Inventors: Hsien-Chieh Hsieh, New Taipei (TW); Pai-Chieh Huang, New Taipei (TW)

(73) Assignee: Wiwynn Corporation, New Taipei (TW)

( * ) Notice: Subject to any disclaimer, the term of this patent is extended or adjusted under 35 U.S.C. 154(b) by 373 days.

(21) Appl. No.: 18/098,714

(22) Filed: Jan. 19, 2023

(65) Prior Publication Data

US 2023/0158317 A1 May 25, 2023

Related U.S. Application Data

(63) Continuation-in-part of application No. 17/109,071, filed on Dec. 1, 2020, now Pat. No. 11,905,747.

(30) Foreign Application Priority Data

Aug. 27, 2020 (TW) .................................. 109129348

(51) Int. Cl.
*A61N 1/375* (2006.01)
*G02B 6/42* (2006.01)

(52) U.S. Cl.
CPC .......... *A61N 1/3754* (2013.01); *G02B 6/4248* (2013.01)

(58) Field of Classification Search
CPC ............................ A61N 1/3754; G02B 6/4248
USPC ......................................... 220/4.02; 174/650
See application file for complete search history.

(56) References Cited

U.S. PATENT DOCUMENTS

| 1,118,435 | A | 11/1914 | Mosler |
| 2,183,448 | A | 12/1939 | Drane |
| 2,460,961 | A | 2/1949 | Wilson |
| 2,875,918 | A | 3/1959 | Baumier |
| 3,087,644 | A | 4/1963 | Hill |
| 3,514,009 | A | 5/1970 | Emery |
| 3,531,823 | A | 10/1970 | Cornelius |

(Continued)

FOREIGN PATENT DOCUMENTS

| CN | 203963317 U | 11/2014 |
| CN | 104343302 A | 2/2015 |

(Continued)

*Primary Examiner* — Orlando E Aviles
*Assistant Examiner* — Niki M Eloshway
(74) *Attorney, Agent, or Firm* — Winston Hsu

(57) ABSTRACT

An airtight device includes a tank, a sink and a feedthrough module. The sink is disposed inside the tank, and an opening is formed on the sink. The feedthrough module is disposed on the opening. The feedthrough module includes a base, a sealing component, a covering component, a transmission component and a plurality of fixing components. A groove is formed on the base. A part of the sealing component is disposed inside the groove. The covering component is assembled with the base and adapted to press the sealing component. A plurality of fixing holes is formed on the covering component. The transmission component is assembled with the covering component. The plurality of fixing components is adapted to insert into the plurality of fixing holes and engage with the base for pressing the sealing component by shortening a distance between the base and the covering component.

20 Claims, 14 Drawing Sheets

(56) References Cited

U.S. PATENT DOCUMENTS

| | | | |
|---|---|---|---|
| 4,381,581 A | 5/1983 | Ludvik | |
| 4,519,519 A | 5/1985 | Meuschke | |
| 5,186,349 A | 2/1993 | Sakamoto | |
| 6,439,415 B1 | 8/2002 | Salim | |
| 6,936,770 B2* | 8/2005 | Takedomi | F16L 5/10 174/650 |
| 7,475,515 B2* | 1/2009 | Machledt | H02G 9/10 220/500 |
| 7,725,190 B2* | 5/2010 | Iyer | A61N 1/3754 607/36 |
| 8,833,806 B2 | 9/2014 | Wang | |
| 10,008,362 B1* | 6/2018 | Sprengers | H01J 37/16 |
| 2001/0022886 A1* | 9/2001 | Cairns | G02B 6/4428 385/138 |
| 2003/0000726 A1* | 1/2003 | Miyakoshi | H02G 3/081 174/650 |
| 2006/0021992 A1 | 2/2006 | Narushima | |
| 2007/0215614 A1* | 9/2007 | Matsui | H05K 5/0069 220/3.2 |
| 2009/0152142 A1 | 6/2009 | Richardson | |
| 2011/0232961 A1* | 9/2011 | Teske | A61N 1/3754 174/650 |
| 2011/0308041 A1 | 12/2011 | Le | |
| 2013/0032391 A1* | 2/2013 | Morioka | A61N 1/375 174/650 |
| 2013/0035733 A1* | 2/2013 | Breyen | A61N 1/3754 174/650 |
| 2014/0254983 A1* | 9/2014 | Moriya | G02B 6/4251 228/175 |
| 2015/0245468 A1* | 8/2015 | Barry | H05K 3/32 174/257 |
| 2016/0124172 A1* | 5/2016 | Miller | G02B 6/4459 385/136 |
| 2018/0182514 A1* | 6/2018 | Sprengers | H02G 3/22 |
| 2019/0134406 A1* | 5/2019 | Dollar | H01G 4/236 |
| 2019/0134407 A1* | 5/2019 | Dollar | H01G 4/224 |

FOREIGN PATENT DOCUMENTS

| | | | | |
|---|---|---|---|---|
| CN | 107569080 | | 1/2018 | |
| CN | 210739117 U | | 6/2020 | |
| CN | 210989662 | | 7/2020 | |
| JP | 2003-262103 | | 9/2003 | |
| JP | 2014041935 A | * | 3/2014 | G02B 6/0005 |
| TW | 451759 | | 8/2001 | |
| TW | 543979 | | 7/2003 | |
| TW | 202208755 A | | 3/2022 | |
| TW | M634706 U | | 11/2022 | |
| WO | 2016/150074 | | 9/2016 | |

* cited by examiner

AIRTIGHT DEVICE AND FEEDTHROUGH MODULE

CROSS REFERENCE TO RELATED APPLICATIONS

This application is a continuation-in-part of U.S. application Ser. No. 17/109,071, filed on Dec. 1, 2020. The content of the application is incorporated herein by reference.

BACKGROUND OF THE INVENTION

1. Field of the Invention

The present invention relates to an airtight device and a feedthrough module, and more particularly, to an airtight device of preventing gaseous matter from leakage and a related feedthrough module.

2. Description of the Prior Art

A conventional airtight apparatus puts an object inside an accommodating space of the housing, and a cover is assembled with the housing to seal the accommodating space, so that a liquid cooling device in the airtight apparatus can cool the object; however, liquid matter of the liquid cooling device is transformed into gaseous matter by heat, and therefore the airtight apparatus applies stable pressure for the cover to assemble the cover with the housing, so as to prevent the gaseous matter from leakage. A transmission module may be arranged through the housing via holes or openings formed on the housing, thereby allowing signal/power transmission. However, the opening or the holes may cause liquid/gas leakage from the housing; besides, the holes on the housing may be designed for a specific type of the transmission module, which results in inconvenience when replacing the module of the specific type with a module of another type.

SUMMARY OF THE INVENTION

The present invention provides an airtight device of preventing gaseous matter from leakage and a related feedthrough module for solving above drawbacks.

According to one embodiment of the present disclosure, an airtight device includes a tank and a feedthrough module. The tank includes a tank body that defines an accommodating space, wherein the tank body includes a lateral wall, wherein an opening is formed on the lateral wall. The feedthrough module is disposed on the opening. The feedthrough module includes a base, a sealing component, a covering component, and at least one transmission component. The base is disposed on the lateral wall, a groove is formed on a surface of the base. A part of the sealing component is disposed inside the groove. The covering component is assembled with the base and adapted to press the sealing component and cover the opening. The at least one transmission component is assembled with the covering component.

According to one embodiment of the present disclosure, a feedthrough module includes a base, a sealing component, a covering component, and at least one transmission component. The base is formed with a groove and a plurality of engaging holes. The sealing component is partially disposed in the groove. The covering component assembled with the base and adapted to press the sealing component, wherein a plurality of fixing holes are formed on the covering component. The at least one transmission component is assembled with the covering component. The plurality of fixing components are adapted to insert into the plurality of fixing holes and engage with the base for uniformly pressing the sealing component.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
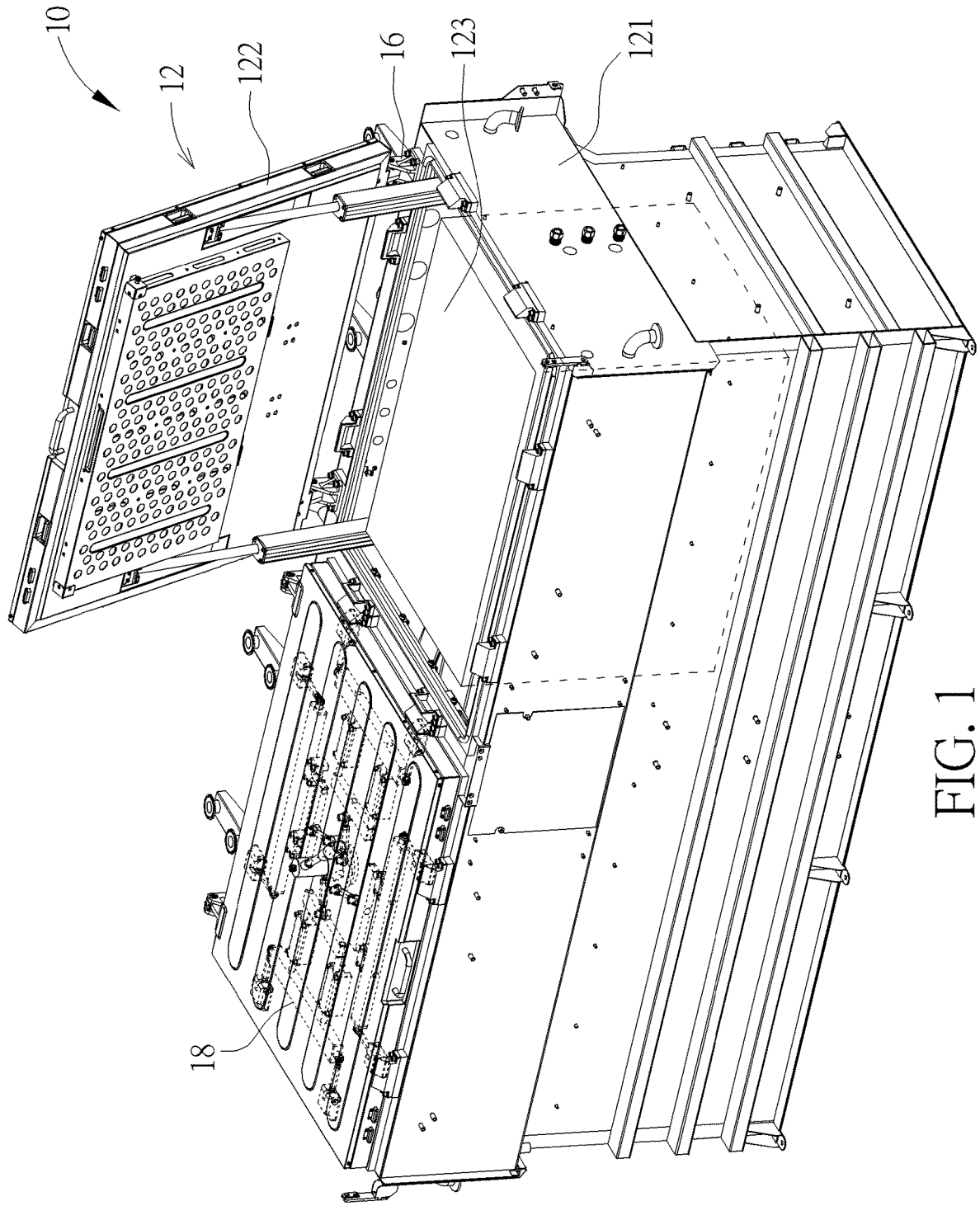
FIG. 1 is a diagram of an airtight device according to an embodiment of the present disclosure.

Please refer to FIG. 1. FIG. 1 is a diagram of an airtight device 10 according to an embodiment of the present disclosure. The airtight device 10 can include a tank 12. The tank 12 comprises a tank body 121, a tank lid 122, a liftable hinge mechanism 16 and a reciprocating engaging mechanism 18. An accommodating space 123 is defined inside the tank body 121. The tank lid 122 is used to cover the tank body 121. The liftable hinge mechanism 16 and the reciprocating engaging mechanism 18 can be respectively disposed between the tank body 121 and the tank lid 122. The tank lid 122 can be connected to the tank body 121 in a rotatable and shiftable manner via the liftable hinge mechanism 16, which means the tank lid 122 can be liftable relative to the tank body 121. With the help of the reciprocating engaging mechanism 18, the tank lid 122 can prevent gaseous matter inside the tank body 121 from leakage. The reciprocating engaging mechanism 18 can simultaneously press and release all sides of the tank lid 122. One or more electronic apparatus (which is not shown in FIG. 1) such as IT gear can be disposed inside the tank body 121 for cooling. The tank lid 122 can be rotated and lifted relative to the tank body 121 for exposing or sealing the electronic apparatus disposed inside the accommodating space 123.

Figure 2:
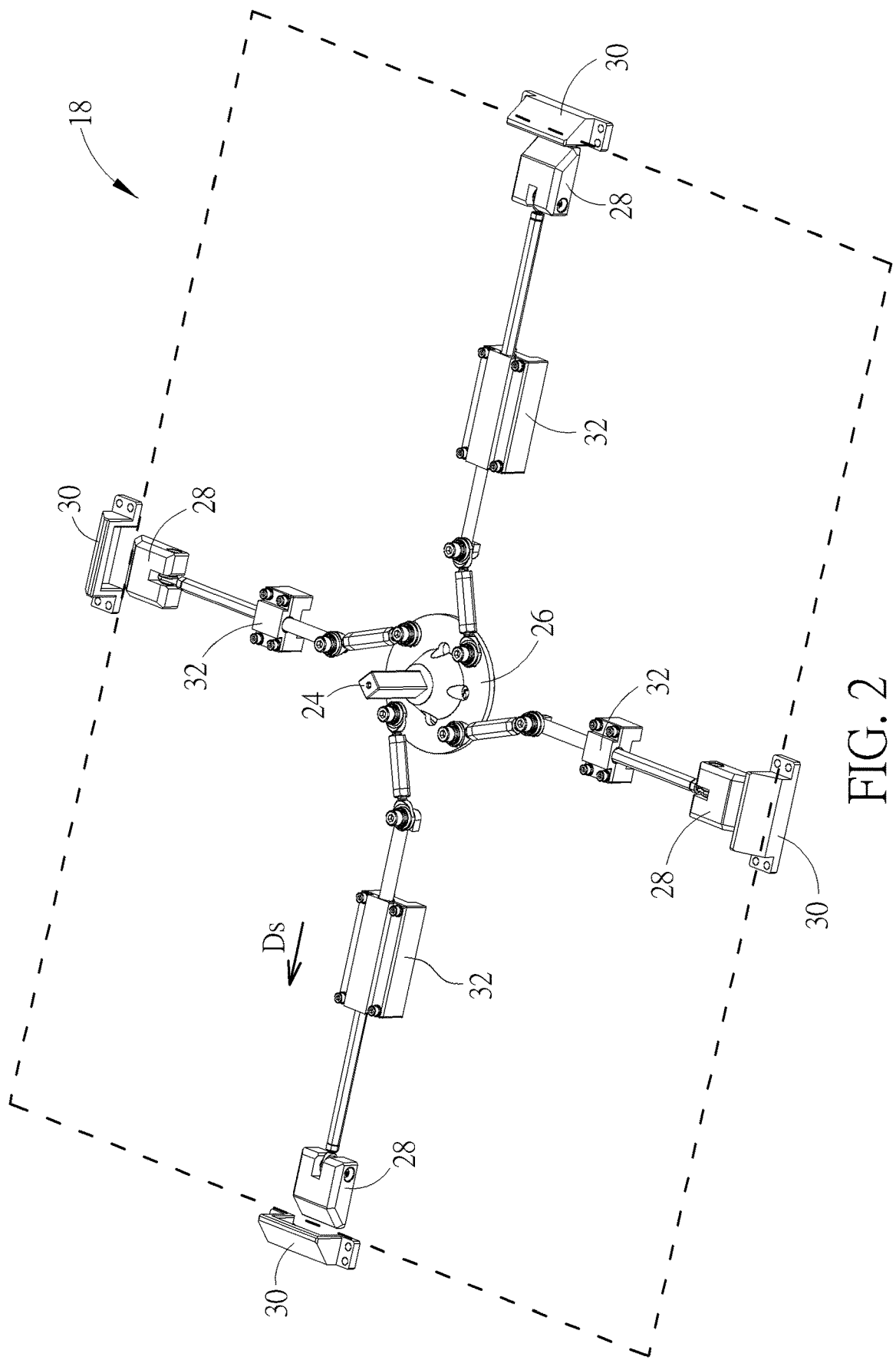
FIG. 2 is a diagram of a reciprocating engaging mechanism according to an embodiment of the present disclosure.

Please refer to FIG. 2. FIG. 2 is a diagram of the reciprocating engaging mechanism 18 according to an embodiment of the present disclosure. The reciprocating engaging mechanism 18 can include a shaft 24, a rotary plate 26, a first engaging component 28, a second engaging component 30 and a linkage module 32. The shaft 24 can be disposed on the tank lid 122. The rotary plate 26 can be rotatably connected to the shaft 24. The first engaging component 28 can be connected to the rotary plate 26 via the linkage module 32. The second engaging component 30 can be disposed on the tank body 121 or the tank 12. The linkage module 32 can include several structural elements connected between the rotary plate 26 and the first engaging component 28. Rotation of the rotary plate 26 can drive the linkage module 32 to move and switch the first engaging component 28 between a locking mode and an unlocking mode, so as to tightly shelter the accommodating space 123 by the tank lid 122 for preventing the gaseous matter inside the accommodating space 123 from leakage.

Figure 3:
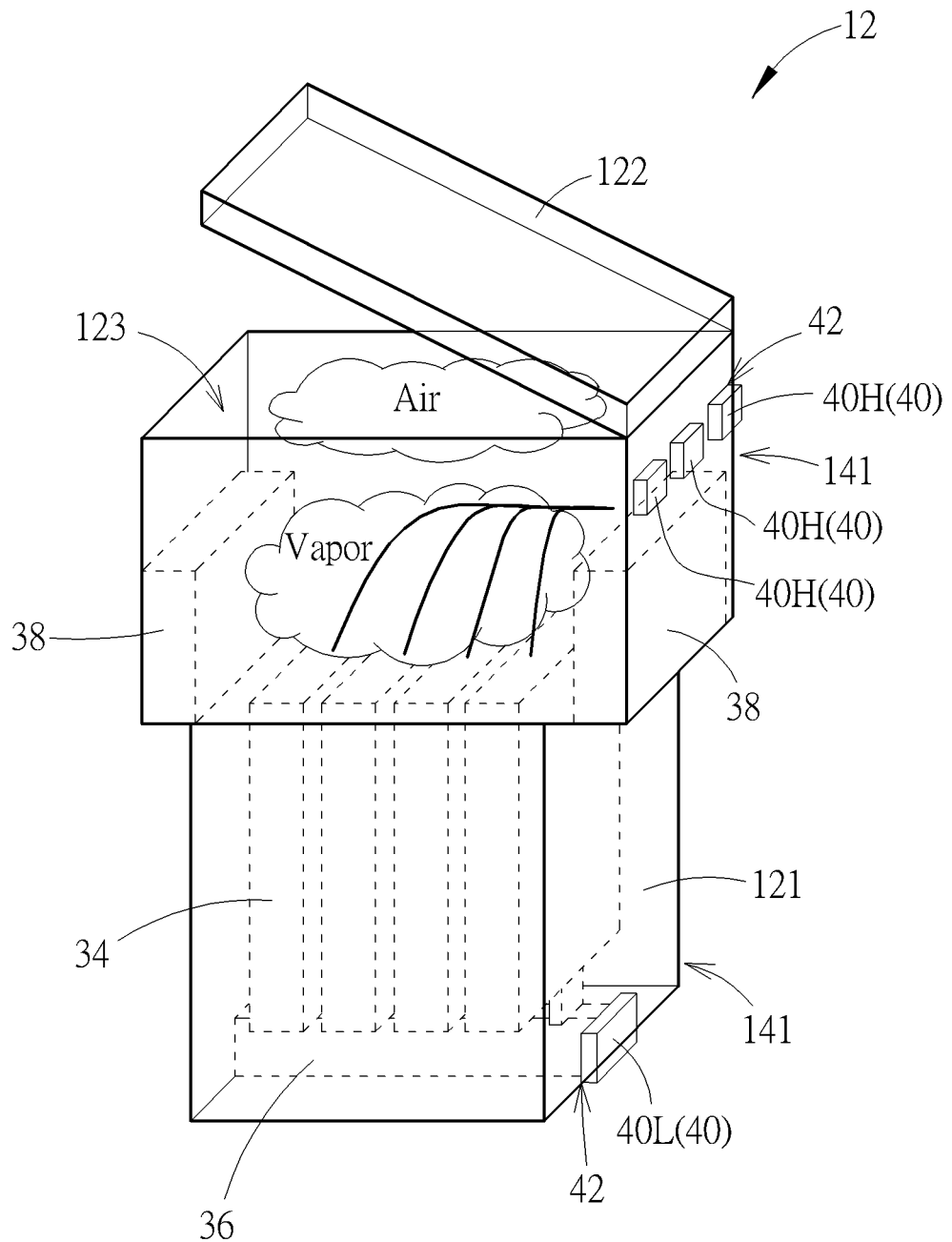
FIG. 3 is a diagram of a part of the airtight device according to the embodiment of the present disclosure.

Please refer to FIG. 3. FIG. 3 is a diagram of a part of the airtight device 10 according to the embodiment of the present disclosure. The tank body 121 is configured to accommodate liquid coolant (which is not marked in the figures), and one or more heat generating device 34 (e.g., the electronic apparatus mentioned as above) disposed inside the tank body 121. During operation, the heat generating device 34 is being immersed by the coolant. The airtight device 10 can further include a power providing module 36, a condenser 38 and at least one feedthrough module 40 (e.g., the feedthrough modules 40H and 40L). The power providing module 36 can be disposed under the heat generating device 34, and connected between the heat generating device 34 and the feedthrough module 40L therefore being connected with external power supply (which is not shown in the figures). The condenser 38 can be disposed above the heat generating device 34 and is not immersed inside the coolant. The tank body 121 can include at least one opening 42 formed on a lateral wall 141 (e.g., a backside wall of the sink) of the tank body 121. A number of the opening 42 can correspond to a number of the feedthrough modules 40H and 40L. The feedthrough modules 40H and 40L can be disposed on the opening 42, and have an airtight and waterproof function to avoid the gaseous matter and the coolant from leakage through the opening 42.

In the illustrated embodiment, the feedthrough modules 40H are arranged above the condenser 38. During operation, the liquid coolant would absorb the heat generated from the heat generating device 34 and then vaporize (i.e., the "vapor" in FIG. 3). The upward-moving vapor would mostly contact and being condensed by the condenser 38 before reaching the feedthrough module 40H, therefore reducing the amount of escaping vapor through the opening 42 when the feedthrough module 40H is removed (e.g., during maintenance). Likewise, the illustrated tank lid 122 is also located above the condenser 38, therefore reducing the amount of escaping vapor when the tank lid 122 is opened (e.g., through operating the reciprocating engaging mechanism as shown in FIG. 2). In the illustrated embodiment, the feedthrough modules 40H are arranged between the tank lid 122 and the condenser 38 along a vertical direction. In some embodiments, the heat generating devices 34 are arranged between the feedthrough module 40 (e.g., the feedthrough modules 40H) for transmitting signal or power and the feedthrough module 40 (e.g., the feedthrough module 40L) for transmitting power along the vertical direction.

Figure 4:
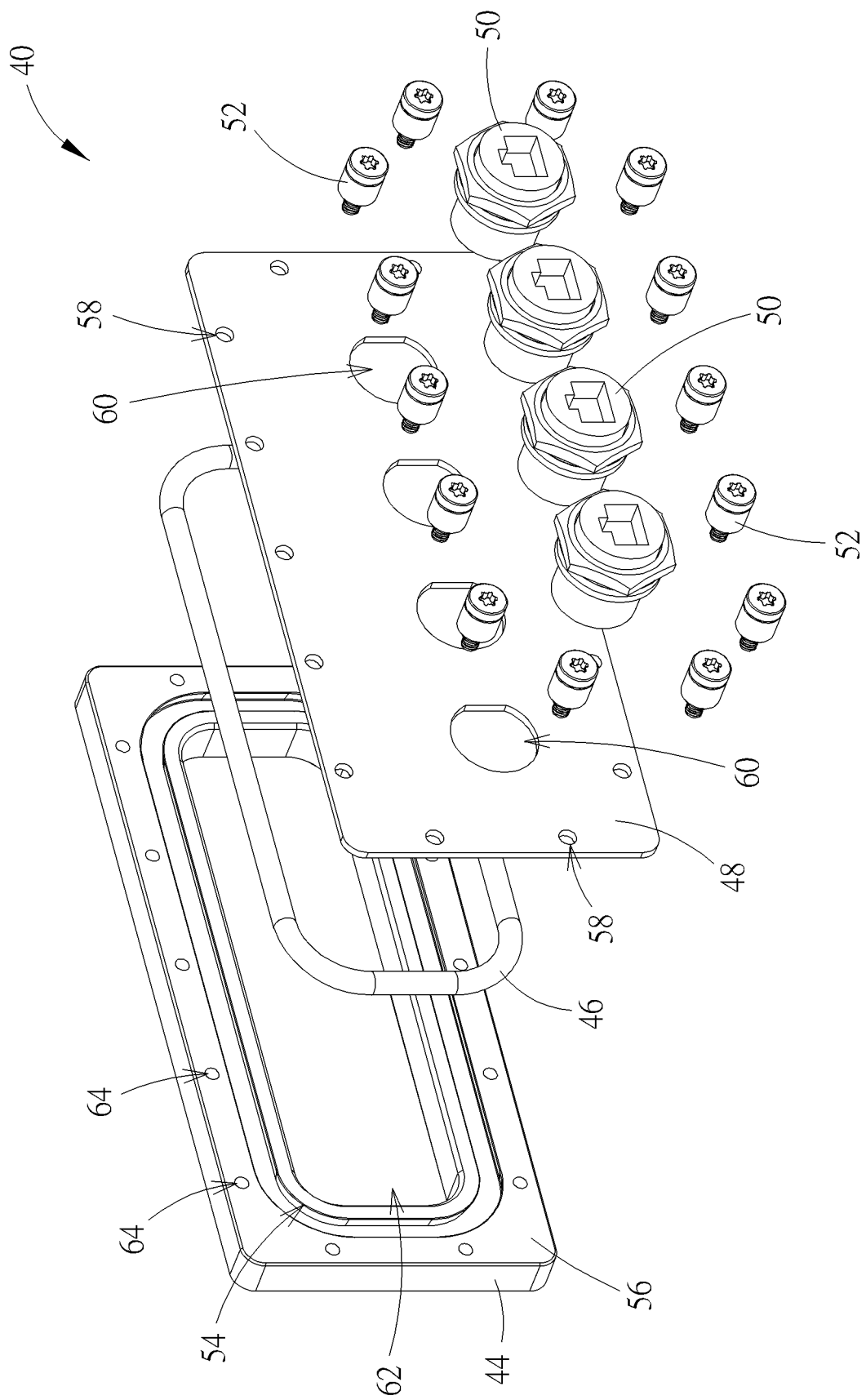
FIG. 4 is an exploded diagram of a feedthrough module according to a first embodiment of the present disclosure.
Figure 5:
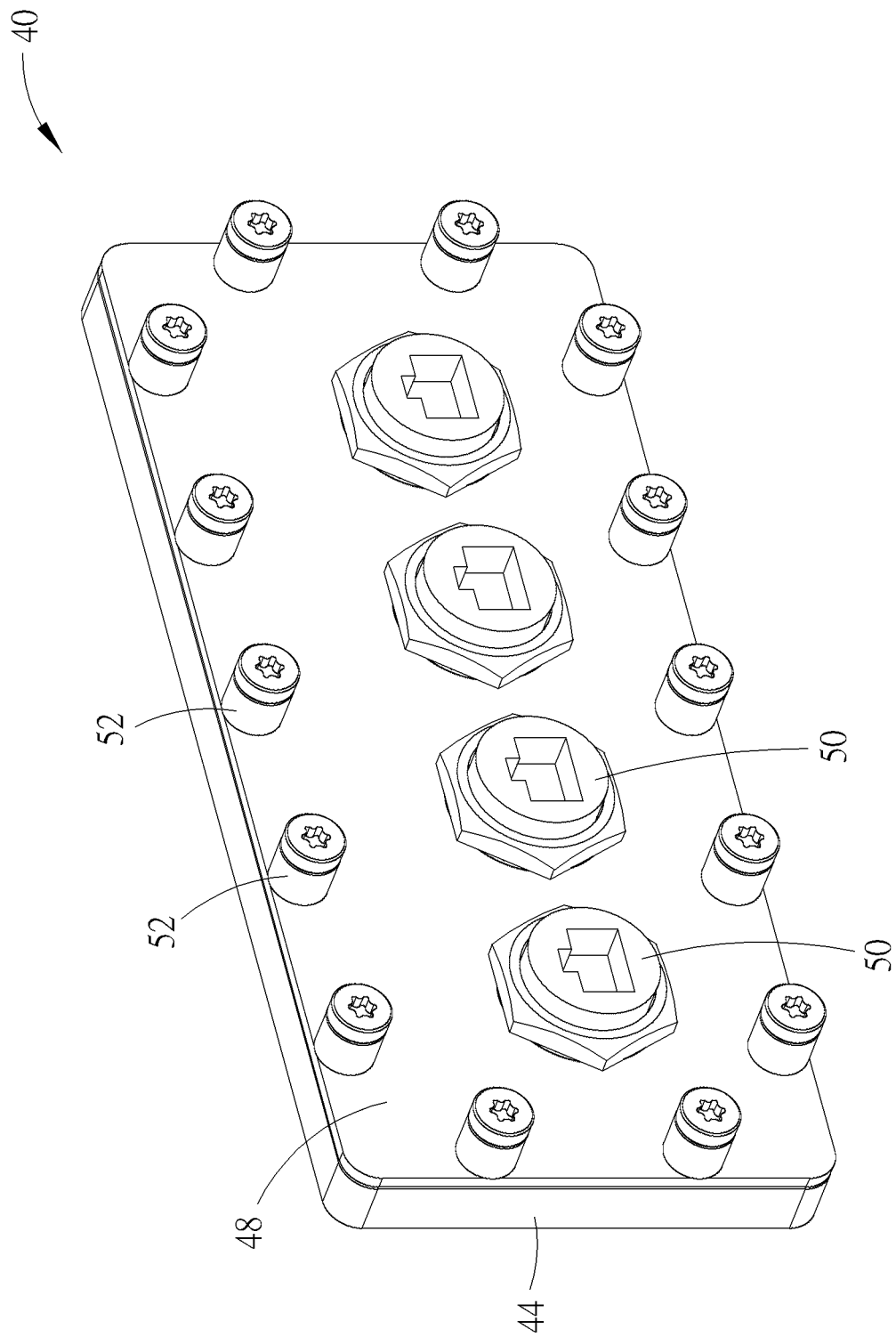
FIG. 5 is an assembly diagram of the feedthrough module according to the first embodiment of the present disclosure.

Please refer to FIG. 4 and FIG. 5. FIG. 4 is an exploded diagram of the feedthrough module 40 according to a first embodiment of the present disclosure. FIG. 5 is an assembly diagram of the feedthrough module 40 according to the first embodiment of the present disclosure. The feedthrough module 40 can include a base 44, a sealing component 46, a covering component 48, at least one transmission component 50 and a plurality of fixing components 52. The base 44 can be disposed on the lateral wall (e.g., the lateral wall 141 in FIG. 3) of the tank body 121, and a groove 54 can be formed on a surface 56 of the base 44 opposite to the tank body 121. The sealing component 46 can be partially disposed inside the groove 54 and be further pressed by the covering component 48. The covering component 48 can be attached to the base 44 and covers the opening (e.g., opening 42) of the tank via the plurality of fixing components 52. The covering component 48 can have a plurality of fixing holes 58 and at least one installing hole 60.

A number of the transmission component 50 can correspond to a number of the installing hole 60. The transmission component 50 can be arranged through the installing hole 60 in an airtight and waterproofing manner, and be electrically connected to the heat generating device 34 or the power providing module 36, which depend on a type of the feedthrough module 40. A number of the fixing components 52 can correspond to a number of the fixing holes 58. One of the plurality of fixing components 52 can be inserted into one of the plurality of fixing holes 58, and be engaged with one of a plurality of engaging holes 64 formed on the surface 56 of the base 44. Therefore, when the plurality of fixing components 52 is uniformly inserted into the plurality of fixing holes 58 and engaged with the plurality of engaging holes 64, the sealing component 46 can be uniformly pressed by the base 44 and the covering component 48 for filling the groove 54, so as to provide the preferred airtight and waterproof function.

In some embodiments, the base 44 is configured to be attached a surface of the lateral wall (e.g., lateral wall 141) opposite to the accommodating space 123 defined by the tank body 121, and the covering component 48 is configured to be attached to the base 44 from outside of the tank body 121. During maintenance, the covering component 48 could be easily removed from outside of the tank body 121 without opening the lid 122 of the tank 12, therefore reducing the amount of escaping vapor. During maintenance, a dummy cover could be further attached to the base 44, easily from outside of the tank 12, such that the opening (e.g., opening 42) is still being covered while the covering component 48 is removed, therefore reducing the amount of escaping vapor. Besides, the groove 54 on the base 44 is shown to be annular and the engaging holes 64 are located outside of an area of the base 44 surrounded by the groove 54. Under such arrangement, even though the pressure of the vapor (e.g., "vapor" in FIG. 3) in the accommodating space 123 is high, the vapor could be blocked by the sealing component 46 before reaching the fixing holes 58 of the covering component 44, thereby significantly reduce the amount of vapor escaping via the fixing holes 58. In fact, the illustrated sealing component 46 disposed in the groove 54 is uniformly surrounded by the engaging holes 64 and being uniformly pressed.

As shown in FIG. 4, a window 62 can be further formed on the base 44. The transmission component 50 which arranged through the installing hole 60 can pass through the window 62 to reach into the accommodating space 123 for electrically connecting with the heat generating device 34 or the power providing module 36. The window 62 can be surrounded by the groove 54, and the groove 54 can be surrounded by the plurality of engaging holes 64, so that the feedthrough module 40 can uniformly press the sealing component 46 by moving the covering component 48 toward the base 44 for shortening a distance between the base 44 and the covering component 48. In the first embodiment, the feedthrough module 40 is disposed on the opening 42 located above the electronic device (e.g., the heat generating device 34 in FIG. 3) and the condenser (e.g., the condenser 38 in FIG. 3), so that the transmission component 50 of the feedthrough module 40 can be electrically connected to the heat generating device 34. In addition, the covering component 48 can be made of metal material, and be optionally coated by an isolation layer in accordance with the design demand.

Figure 6:
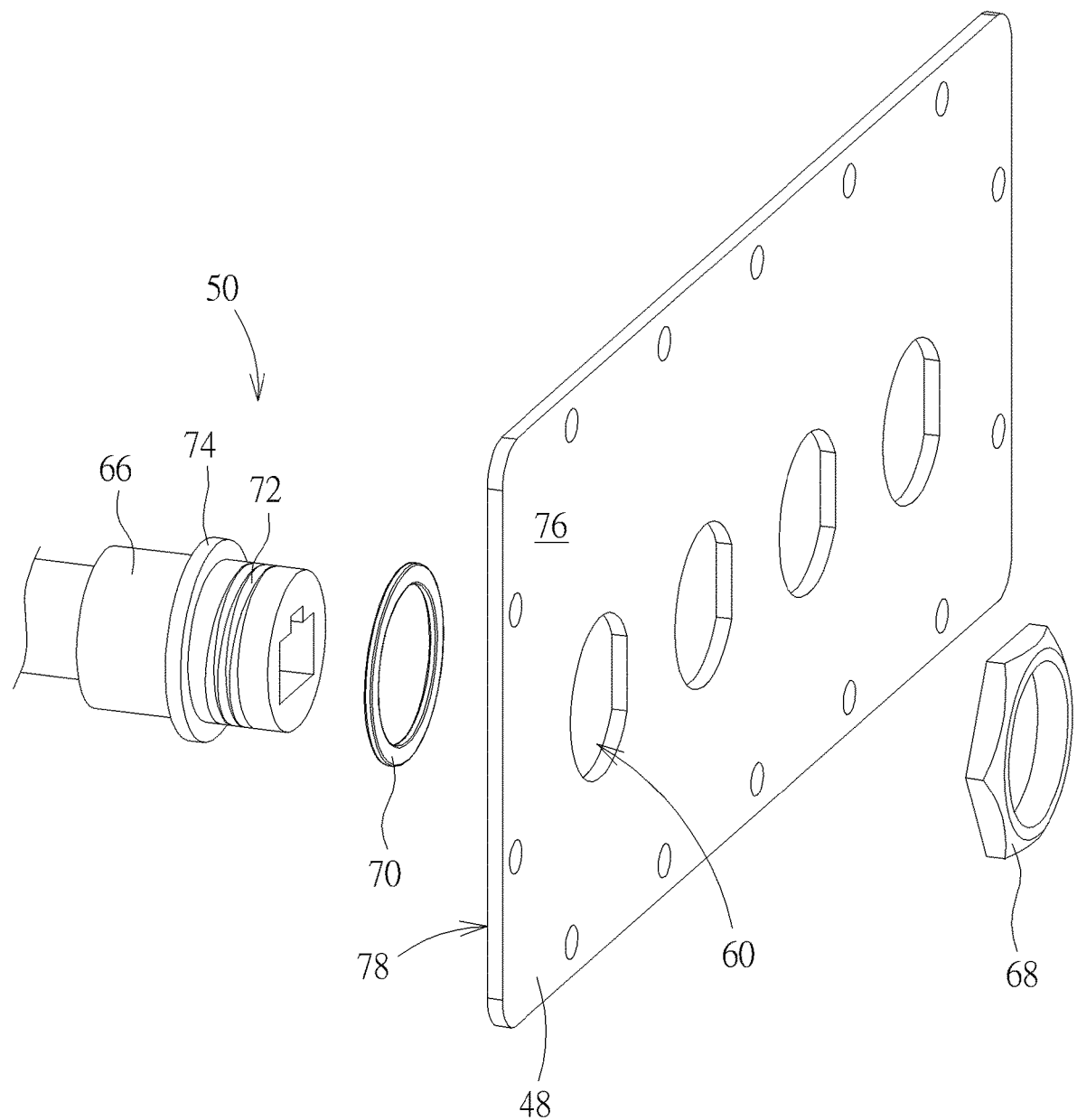
FIG. 6 is an exploded diagram of the transmission component in another type according to the first embodiment of the present disclosure.
Figure 7:
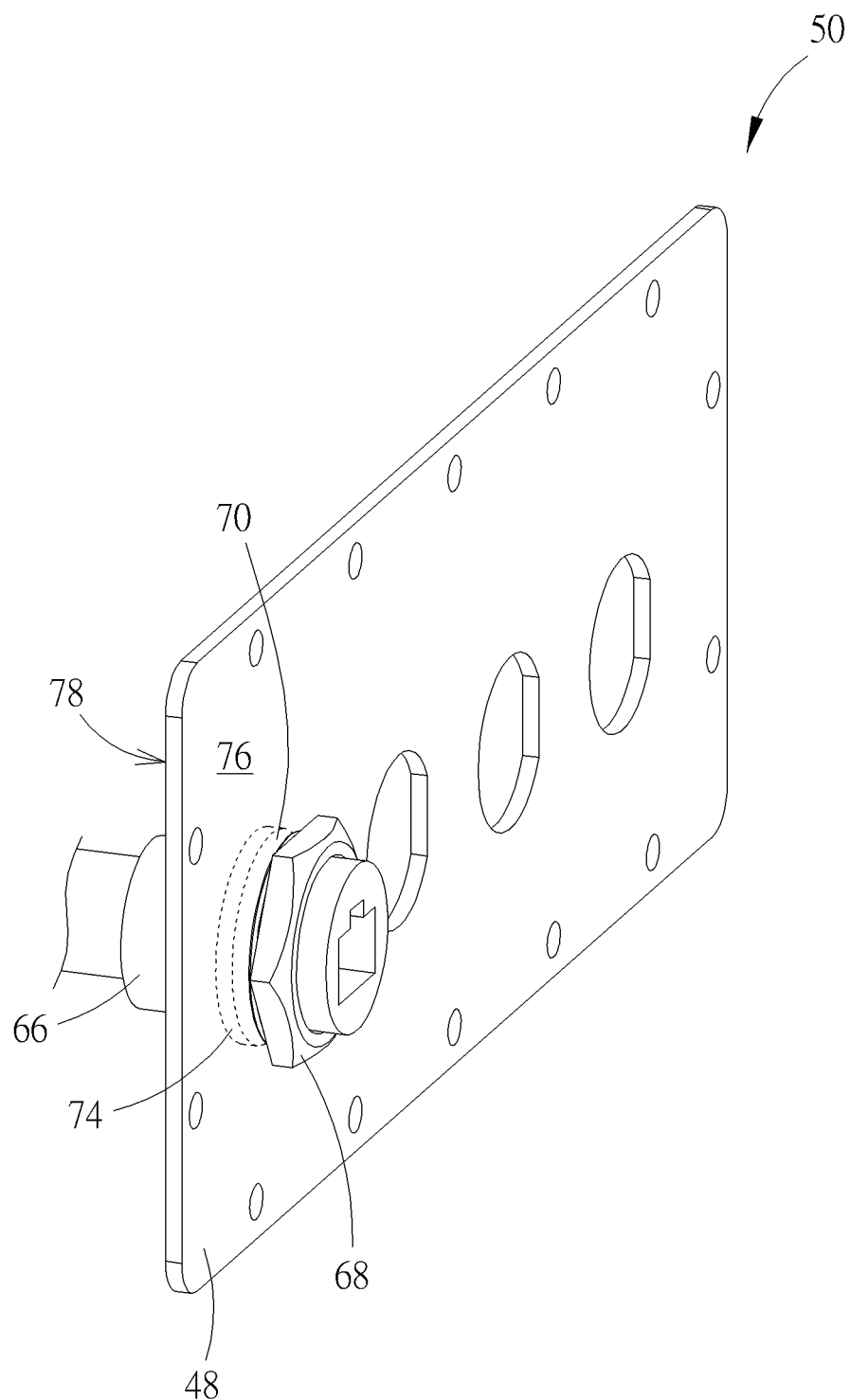
FIG. 7 is an assembly diagram of the transmission component according to the first embodiment of the present disclosure.

Please refer to FIG. 6 and FIG. 7. FIG. 6 is an exploded diagram of the transmission component 50 in another type according to the first embodiment of the present disclosure. FIG. 7 is an assembly diagram of the transmission component 50 according to the first embodiment of the present disclosure. The transmission component 50 can include a cable 66, a nut 68 and a sealing element 70. The cable 66 can have a thread structure 72 and an annular portion 74. The annular portion 74 can be distant from or adjacent to the thread structure 72. One end of the cable 66 can insert into the installing hole 60, and the other end of the cable 66 can extend into the accommodating space 123 for connecting the heat generating device 34 or the power providing module 36. The nut 68 can be engaged with the thread structure 72 and press one surface 76 (e.g., opposite to the accommodating space 123) of the covering component 48. The cable 66 can be locked with the nut 68 and therefore the annular portion 74 can abut toward another surface 78 (e.g., facing the accommodating space 123) of the covering component 48 opposite to the nut 68. A sealing element 70 can be disposed between the annular portion 74 of the cable 66 and the surface 78 of the covering component 48 by pressure of the covering component 48 and the annular portion 74 for the preferred airtight and waterproof function, such as the embodiment shown in FIG. 6.

In the embodiment shown in FIG. 6, the sealing element 70 is clipped by the covering component 48 and the annular portion 74. Since the surface 78 of the covering component 48 provides a sufficient contact area for abutting against the sealing element 70, the sealing element 70 can be made with a sufficiently large size even though a size of the nut 68 is being reduced. By reducing the size of the nut 68, a number of the installing holes 60 formed on the covering component 48 can be increased, thereby increasing the number of transmission module.

Figure 8:
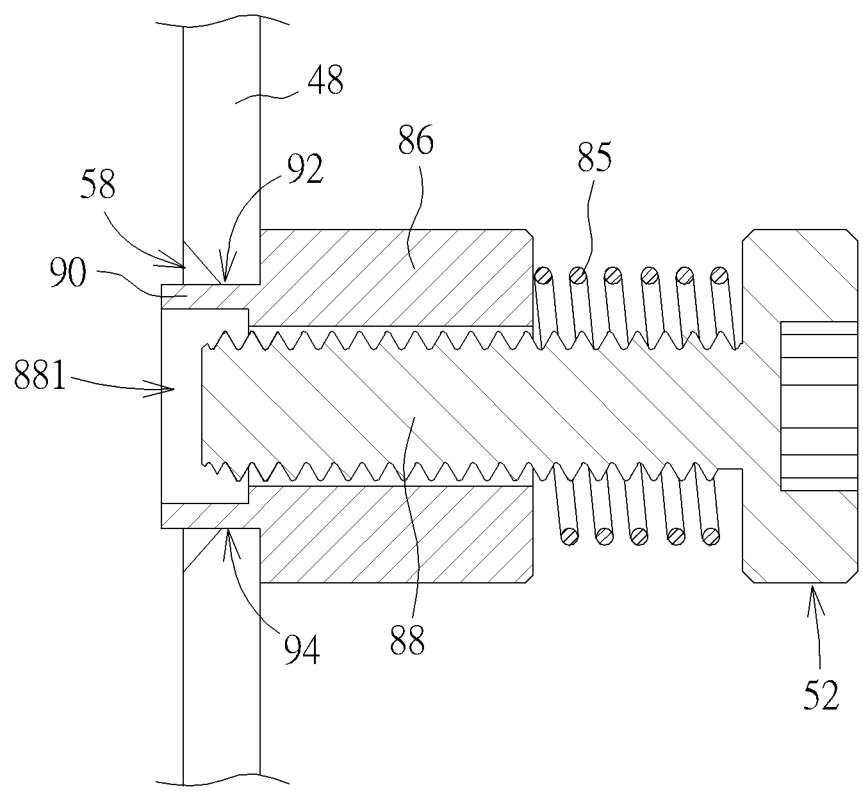
FIG. 8 is a sectional view of a part of a covering component and a fixing component in one operation mode according to the first embodiment of the present disclosure.
Figure 9:
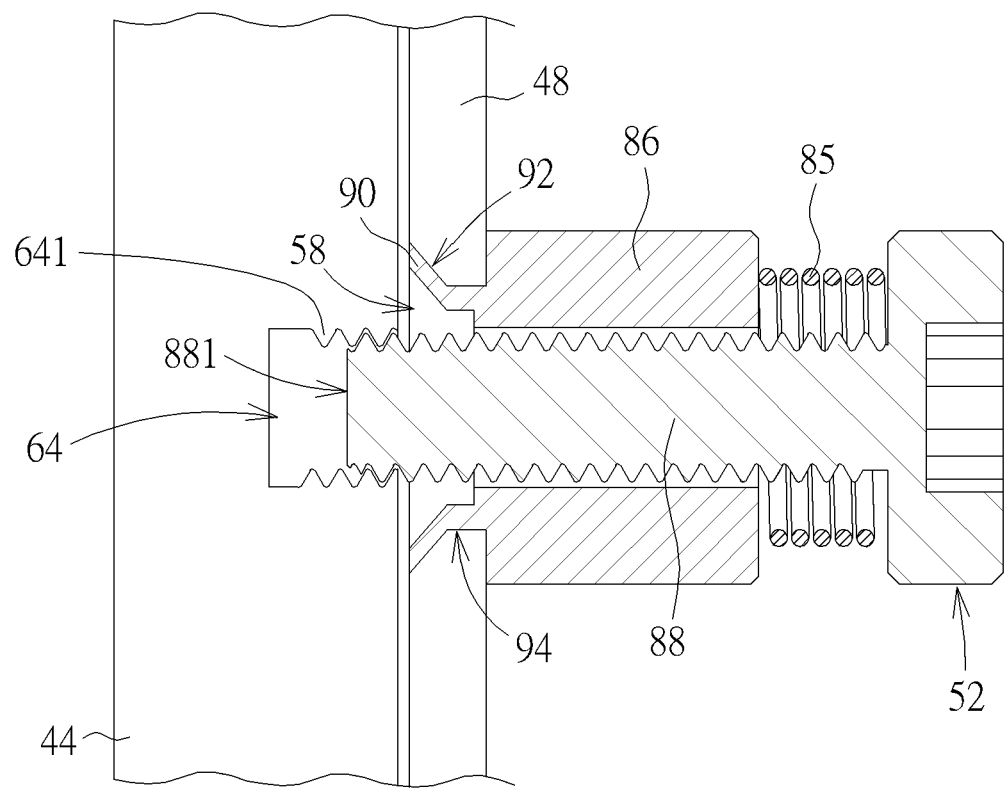
FIG. 9 is a sectional view of the part of the covering component and the fixing component in another operation mode according to the first embodiment of the present disclosure.

Please refer to FIG. 8 and FIG. 9. FIG. 8 and FIG. 9 are sectional views of a part of the covering component 48 and the fixing component 52 in different operation modes according to the first embodiment of the present disclosure. The fixing component 52 can include a resilient element 85 (e.g., a spring), a bushing 86 and a screwing body 88. Two opposite ends of the resilient element 85 can be respectively connected to the bushing 86 and a top of the screwing body 88. The bushing 86 can be inserted into the fixing hole 58 formed on the covering component 48, and a protrusion 90 of the bushing 86 can be protruded from the fixing hole 58. Then, the protrusion 90 can be pressed and deformed by an external force to engage with a depression 92 formed on an inner surface 94 of the fixing hole 58 for a riveting function. In response to engagement of the bushing 86 and the depression 92, the screwing body 88 can be engaged with the engaging hole 64 of the base 44 and the covering component 48 can be tightly assembled with each other via the fixing component 52 to provide the preferred airtight and waterproof function.

As shown in FIG. 8, when the resilient element 85 is not compressed, a front end 881 of the screwing body 88 does not protrude from the fixing hole 58 on the covering component 48, so as to avoid the fixing component 52 and the base (e.g., the base 44 in FIG. 9) from structural interference. The screwing body 88 cannot be separated from the bushing 86 via connection of the resilient element 85.

As shown in FIG. 9, the fixing component 52 is pushed to the left and the resilient element 85 is being compressed. The front end of the screwing body 88 can be engaged with a thread structure 641 of the engaging hole 64 formed on the base 44. An inner surface of the bushing 86 may not have the thread structure to provide rapid and convenient advantages of engaging the fixing component 52 with the base 44.

Figure 10:
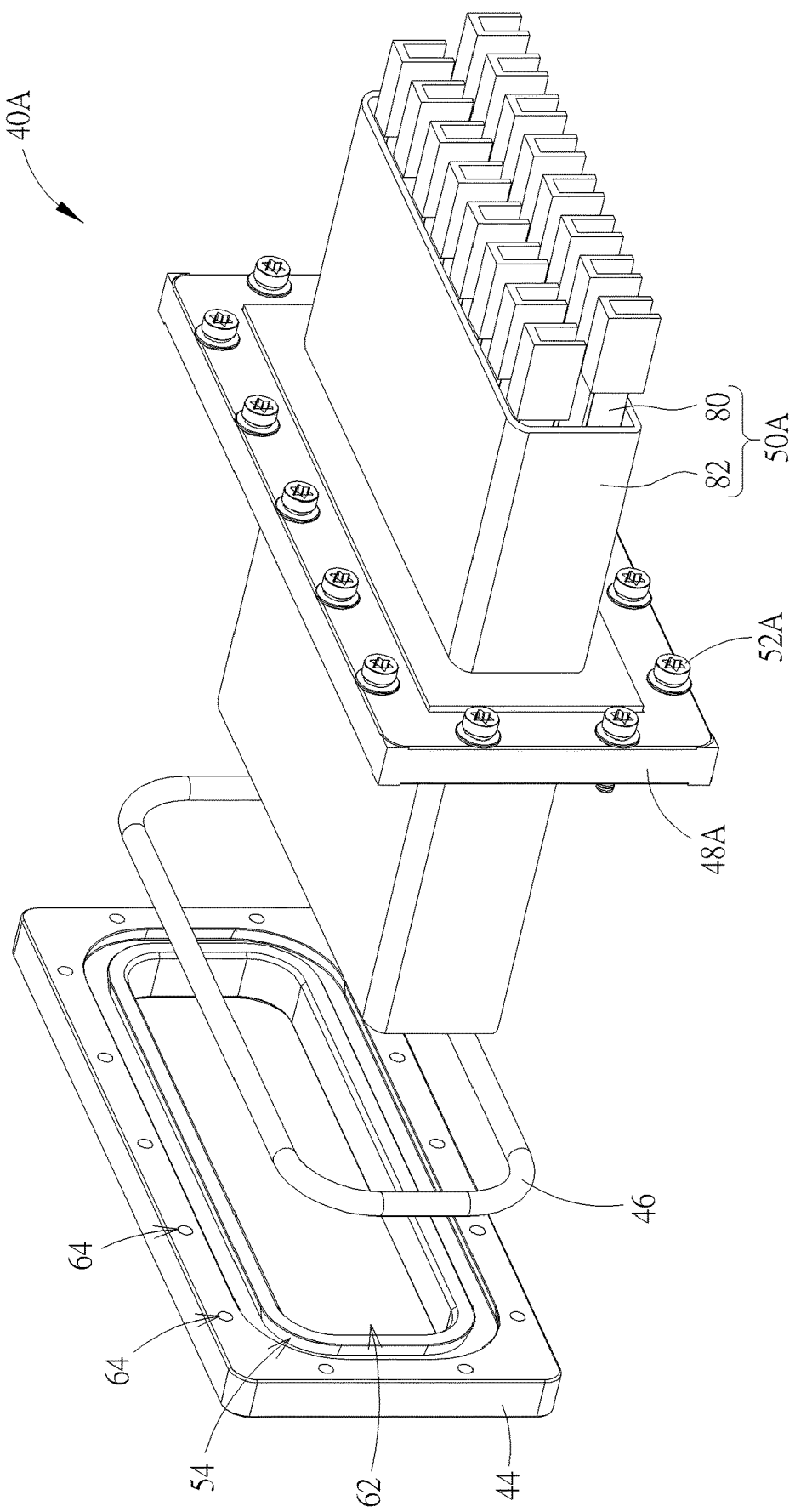
FIG. 10 is an exploded diagram of the feedthrough module according to a second embodiment of the present disclosure.
Figure 11:
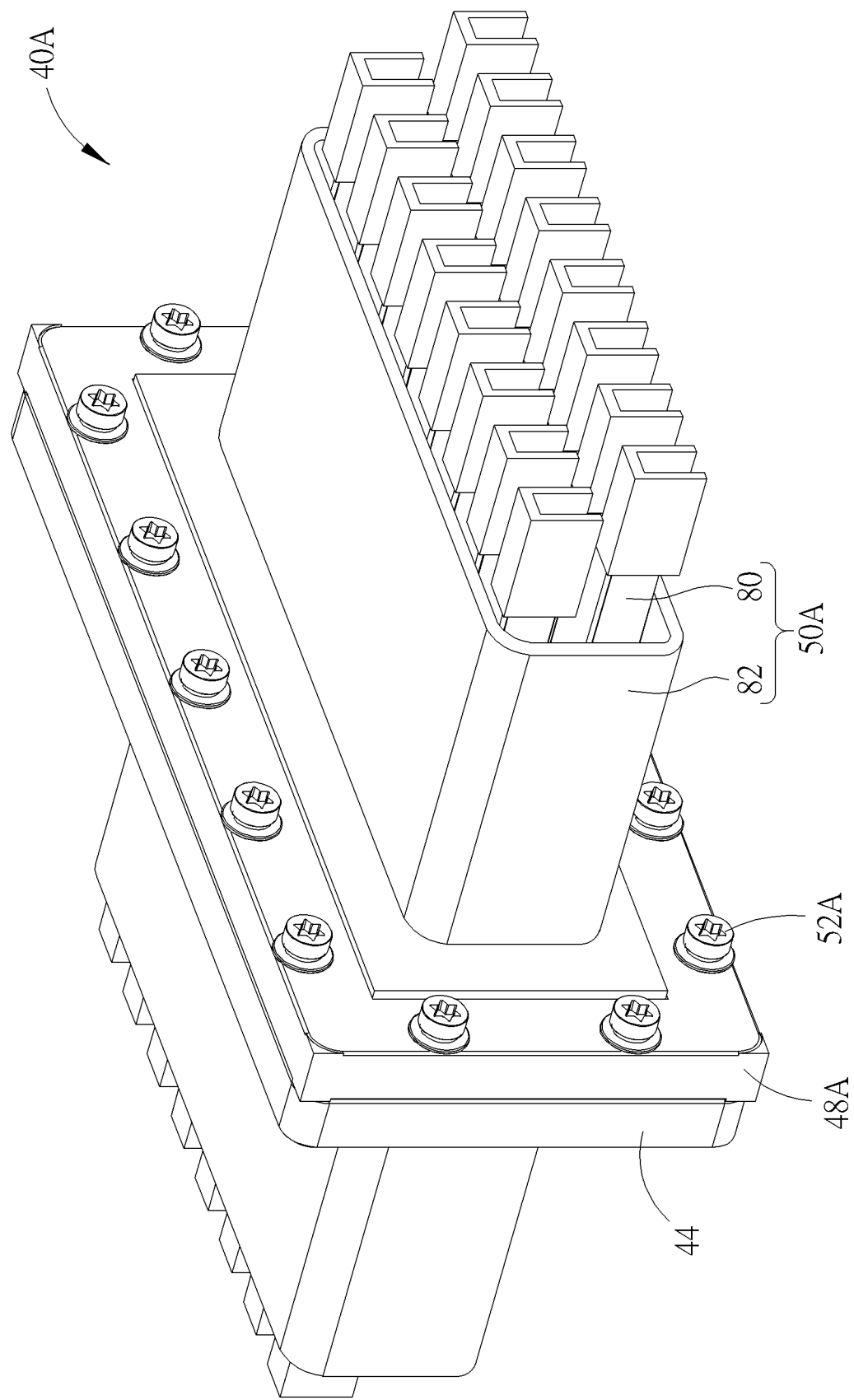
FIG. 11 is an assembly diagram of the feedthrough module according to the second embodiment of the present disclosure.
Figure 12:
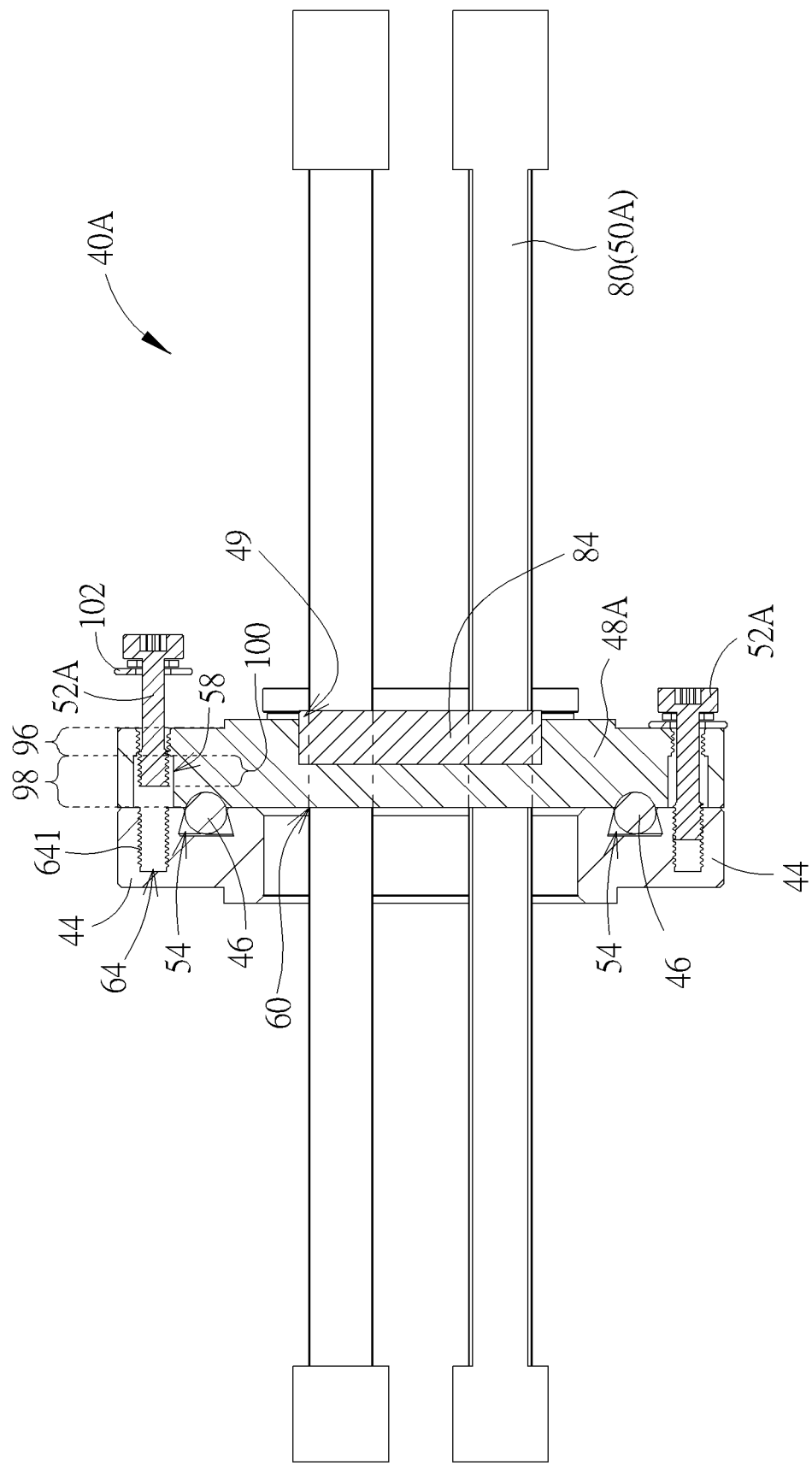
FIG. 12 is a sectional view of the feedthrough module according to the second embodiment of the present disclosure.

Please refer to FIG. 10 to FIG. 12. FIG. 10 is an exploded diagram of the feedthrough module 40A according to a second embodiment of the present disclosure. FIG. 11 is an assembly diagram of the feedthrough module 40A according to the second embodiment of the present disclosure. FIG. 12 is a sectional view of the feedthrough module 40A according to the second embodiment of the present disclosure. In the second embodiment, elements having the same numerals as ones of the first embodiment have the same structures and functions, and a detailed description is omitted herein for simplicity. The feedthrough module 40A can include the base 44, the sealing component 46, a covering component 48A, a transmission component 50A and a plurality of fixing components 52A. The transmission component 50A can be inserted into and engaged with the installing hole 60 of the covering component 48A in the airtight and waterproofing manner.

In the second embodiment, the transmission component 50A can include an array of several cables 80, a case 82 and a sealing element 84. An adapter of the cable 80 can be supported by the case 82 connected with the covering component 48A. The sealing element 84 can be disposed around the cable 80 and filled within a sunken portion 49 of the covering component 48A for the preferred airtight and waterproof function. The sunken portion 49 can be located on an area of the covering component 48 where the installing hole 60 and the cable 80 is arranged. The sealing element 84 can be epoxy. The feedthrough module 40A can be disposed on the opening 42 located above the condenser 38, and the transmission component 50A of the feedthrough module 40A can be electrically connected with the heat generating device 34.

A thickness of the covering component 48A can be sufficiently large (e.g., greater than a thickness of the covering component 48 in the first embodiment), so that the fixing hole 58 on the covering component 48A can include an inner thread portion 96 and a non-thread portion 98 adjacent to each other. A length of the non-thread portion 98 of the fixing hole 58 can be greater than a length of an outer thread portion 100 of the fixing component 52A. A length of the thread structure 641 of the engaging hole 64 is configured greater than the length of the outer thread portion 100 of the fixing component 52A. The inner thread portion 96 can be used to block the outer thread portion 100 to prevent the fixing component 52A from being separated from the fixing hole 58. The outer thread portion 100 can be stayed inside the fixing hole 58 when the fixing component 52A is disengaged from the engaging hole 64. A washer 102 can be pressed by the fixing component 52A to abut against the covering component 48A for the preferred airtight and waterproof function.

Figure 13:
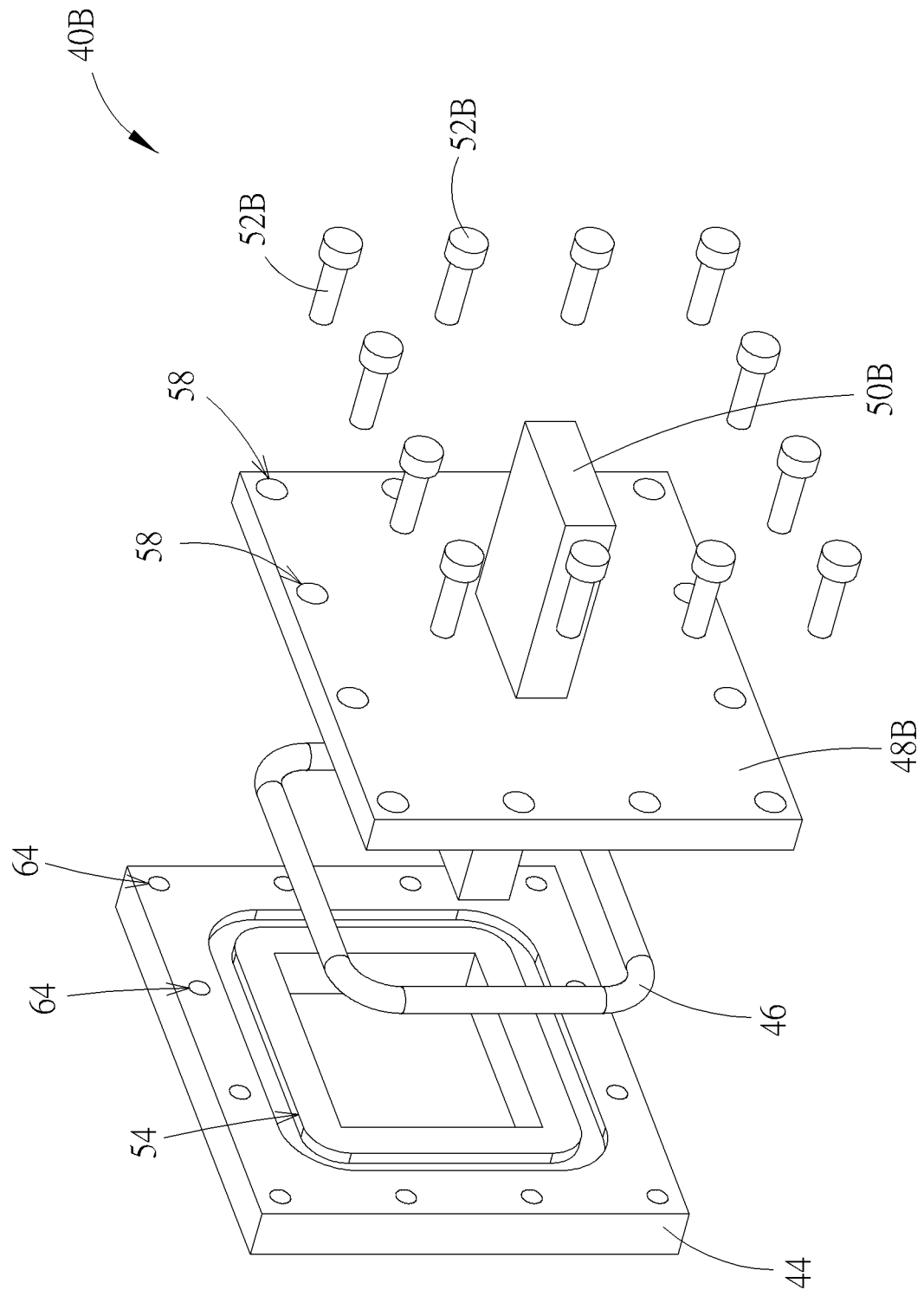
FIG. 13 is an exploded diagram of the feedthrough module according to a third embodiment of the present disclosure.
Figure 14:
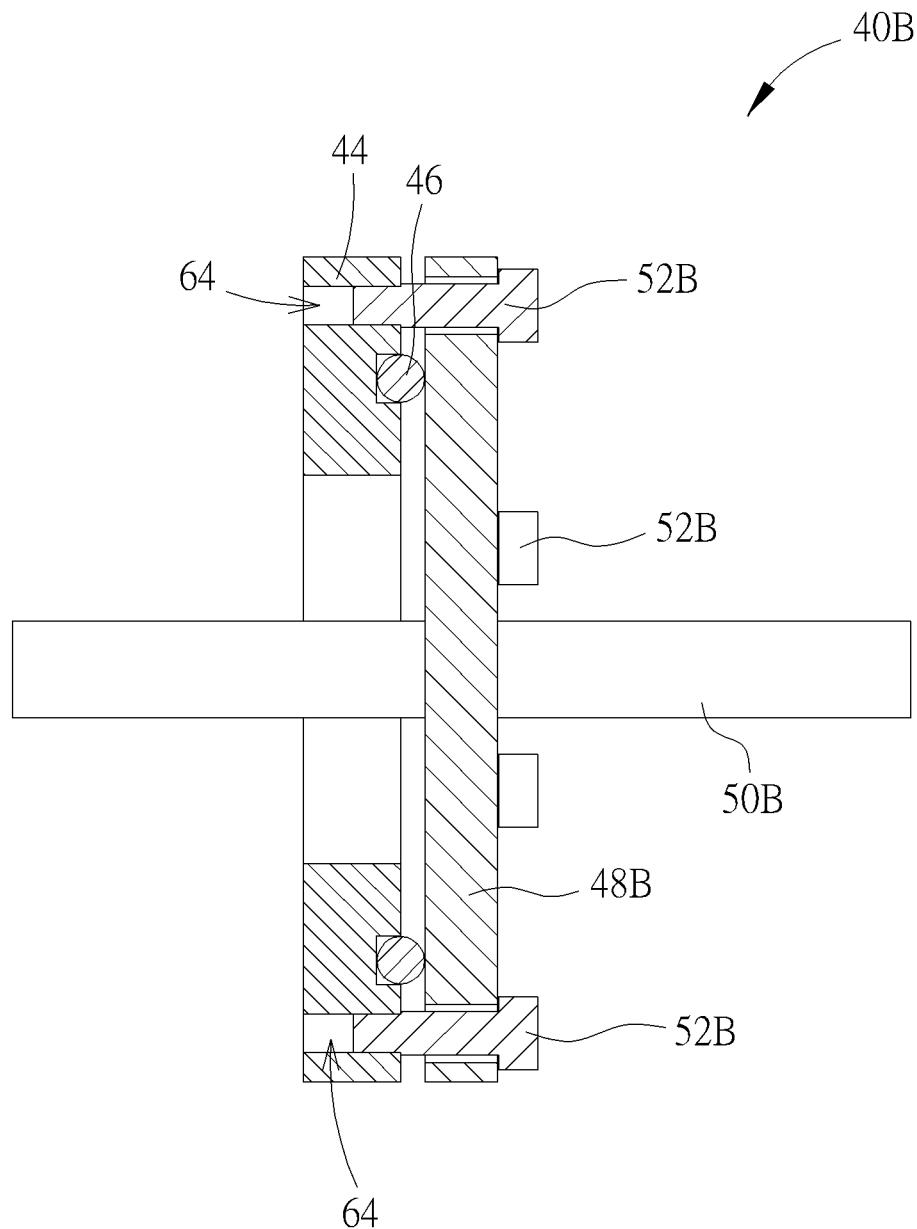
FIG. 14 is an assembly diagram of the feedthrough module according to the third embodiment of the present disclosure.

Please refer to FIG. 13 and FIG. 14. FIG. 13 is an exploded diagram of the feedthrough module 40B according to a third embodiment of the present disclosure. FIG. 14 is an assembly diagram of the feedthrough module 40B according to the third embodiment of the present disclosure. In the third embodiment, elements having the same numerals as ones of the foresaid embodiment have the same structures and functions, and the detailed description is omitted herein for simplicity. The feedthrough module 40B can include the base 44, the sealing component 46, a covering component 48B, a transmission component 50B and a plurality of fixing components 52B. The feedthrough module 40B can be disposed on the opening 42 located under the heat generating device 34, and can be electrically connected to the external power supply.

In the third embodiment, the covering component 48B and the transmission component 50B can be made of the same conductive material. For example, the transmission component 50B can be integrated with the covering component 48B monolithically. The covering component 48B can be further coated by the isolation layer. The fixing component 52B can be inserted into the fixing hole 58 on the covering component 48B and engaged with the engaging hole 64 on the base 44. The sealing component 46 can be disposed between the base 44 and the covering component 48B, and can be pressed to fill with the groove 54 on the base 44 when the fixing component 52B is tightly engaged with the engaging hole 64.

In conclusion, the feedthrough module of the airtight device in the present disclosure can utilize the plurality of fixing components to lock the base and the covering component, and the sealing component can be located between the base and the covering component and partly inside the groove on the base. The plurality of fixing components can be separately engaged with the engaging holes on the base in the symmetrical and staggered manner, so that the sealing component can be uniformly pressed and deformed to avoid the gaseous matter in the sink from leakage through unexpected space between the base and the covering component. The fixing component can be designed in accordance with the thickness of the covering component. The transmission component can be designed as a connector, a cable array or a busbar, which depends on an actual demand. The feedthrough module which provides the airtight function can be disposed on the opening above the heating device and not immersed inside the coolant, and the feedthrough module which provides the waterproofing function can be disposed on the opening under the heating device and immersed inside the coolant.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An airtight device, comprising:
    a tank configured to accommodate liquid coolant and related gaseous matter and comprising a tank body that defines an accommodating space, wherein the tank body comprises a lateral wall, and an opening is formed on the lateral wall; and
    a feedthrough module disposed on the opening, the feedthrough module comprising:
        a base disposed on the lateral wall, a groove being formed on a surface of the base;
        a sealing component, a part of the sealing component being disposed inside the groove;
        a covering component assembled with the base and adapted to press the sealing component and cover the opening; and
        at least one transmission component assembled with the covering component;
        wherein the feedthrough module is set on at least one of position arranged above a condenser inside the accommodating space and position located under a heat generating device inside the tank body.

2. The airtight device of claim 1, wherein at least one installing hole is formed on the covering component, and the at least one transmission component is arranged through the at least one installing hole to assemble with the covering component.

3. The airtight device of claim 1, wherein the at least one transmission component is integrated with the covering component monolithically.

4. The airtight device of claim 1, wherein the base is formed with a window surrounded by the groove, the at least one transmission component reaches into the accommodating space via the window and the opening.

5. The airtight device of claim 4, wherein the base is formed with a plurality of engaging holes; the covering component is formed with a plurality of fixing holes corresponding to the engaging holes; the feedthrough module further comprises a plurality of fixing components adapted to insert into the plurality of fixing holes and the plurality of engaging holes so as to engage with the base for uniformly pressing the sealing component.

6. The airtight device of claim 5, wherein the groove is surrounded by the plurality of engaging holes.

7. The airtight device of claim 5, wherein each of the plurality of fixing components comprises a bushing, a protrusion of the bushing is engaged with a depression formed inside an inner surface of each of the plurality of fixing holes.

8. The airtight device of claim 5, wherein each of the plurality of fixing holes on the covering component comprises an inner thread portion and a non-thread portion adjacent to each other, a length of the non-thread portion is greater than a length of an outer thread portion of each of the plurality of fixing components.

9. The airtight device of claim 8, wherein a length of a thread structure of the engaging hole of the base is configured greater than the length of a thread portion of the fixing components.

10. The airtight device of claim 8, wherein the each of the plurality of fixing components comprises a washer adapted to abut against the covering component.

11. The airtight device of claim 1, wherein the covering component is made of conductive material and further coated by an isolation layer.

12. The airtight device of claim 1, wherein the at least one transmission component comprises a cable and a nut, the cable comprises a thread structure, the cable inserts into at least one installing hole formed on the covering component and extends into the accommodating space, the nut is engaged with the thread structure and adapted to press a surface of the covering component opposite to the accommodating space.

13. The airtight device of claim 12, wherein the at least one transmission component further comprises a sealing element disposed between an annular portion of the cable and a surface of the covering component opposite to the accommodating space.

14. The airtight device of claim 1, wherein the at least one transmission component comprises a cable and a sealing element, the cable is inserted into at least one installing hole formed on the covering component; the sealing element is disposed around the cable.

15. The airtight device of claim 1, wherein the tank further comprises a tank lid, the airtight device further comprises a reciprocating engaging mechanism disposed on the tank lid and adapted to constrain a movement of the tank lid relative to the tank body, the reciprocating engaging mechanism comprises:
 a shaft disposed on the tank lid;
 a rotary plate rotatably disposed on the shaft;
 a first engaging component;
 a second engaging component disposed on the tank body; and
 a linkage module connected between the rotary plate and the first engaging component, rotation of the rotary plate driving the linkage module to move and switch the first engaging component between a locking mode and an unlocking mode, so as to tightly shelter the accommodating space of the tank body by the tank lid for preventing the gaseous matter inside the sink from leakage.

16. The airtight device of claim 1, wherein the feedthrough module is arranged above the condenser inside the tank.

17. The airtight device of claim 16, wherein the feedthrough module is arranged between a tank lid of the tank and the condenser inside the tank.

18. The airtight device of claim 1, wherein the base of the feedthrough module is disposed on a surface of the lateral wall opposite to the accommodating space; the covering component is configured to be assembled with the base from outside of the tank body.

19. A feedthrough module, comprising:
 a base, formed with a groove and a plurality of engaging holes;
 a sealing component, partially disposed in the groove;
 a covering component assembled with the base and adapted to press the sealing component, wherein a plurality of fixing holes are formed on the covering component;
 at least one transmission component assembled with the covering component; and
 a plurality of fixing components adapted to insert into the plurality of fixing holes and the plurality of engaging holes; and
 the plurality of fixing components adapted to insert into the plurality of fixing holes and engage with the base for uniformly pressing the sealing component, a length of a thread structure of each engaging hole of the base being configured greater than a length of a thread portion of each fixing component.

20. The feedthrough module of claim 19, wherein the groove is annular; the engaging holes are located outside of an area on a surface of the base surrounded by the groove.

* * * * *